(12) United States Patent
Singer

(10) Patent No.: US 11,471,404 B2
(45) Date of Patent: *Oct. 18, 2022

(54) COMPOSITION AND METHOD FOR ORALLY ADMINISTERING ONE OR MORE ACTIVE AGENTS TO A PET

(71) Applicant: Société des Produits Nestlé S.A., Vevey (CH)

(72) Inventor: Ryan H. Singer, New York, NY (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 22 days.

This patent is subject to a terminal disclaimer.

(21) Appl. No.: 17/125,296

(22) Filed: Dec. 17, 2020

(65) Prior Publication Data

US 2021/0137832 A1    May 13, 2021

Related U.S. Application Data

(63) Continuation of application No. 16/537,131, filed on Aug. 9, 2019, now Pat. No. 10,898,433, which is a
(Continued)

(51) Int. Cl.

| | | |
|---|---|---|
| A61K 9/00 | (2006.01) | |
| A61K 8/19 | (2006.01) | |
| A61K 8/24 | (2006.01) | |
| A61K 31/7008 | (2006.01) | |
| A61K 31/726 | (2006.01) | |
| A61K 31/10 | (2006.01) | |
| A61K 31/728 | (2006.01) | |
| A61K 31/455 | (2006.01) | |
| A61K 31/198 | (2006.01) | |
| A61K 31/51 | (2006.01) | |
| A61K 31/4415 | (2006.01) | |
| A61K 31/714 | (2006.01) | |
| A61Q 11/00 | (2006.01) | |
| A23K 20/147 | (2016.01) | |
| A23K 20/158 | (2016.01) | |
| A23K 20/163 | (2016.01) | |
| A23K 20/179 | (2016.01) | |
| A23K 50/20 | (2016.01) | |
| A23K 50/40 | (2016.01) | |
| A23K 50/42 | (2016.01) | |
| A23K 10/28 | (2016.01) | |
| A23K 20/00 | (2016.01) | |
| A23K 20/10 | (2016.01) | |

(Continued)

(52) U.S. Cl.
CPC ............ *A61K 9/0056* (2013.01); *A23G 4/00* (2013.01); *A23K 10/28* (2016.05); *A23K 20/00* (2016.05); *A23K 20/10* (2016.05); *A23K 20/121* (2016.05); *A23K 20/147* (2016.05); *A23K 20/158* (2016.05); *A23K 20/163* (2016.05); *A23K 20/179* (2016.05); *A23K 50/20* (2016.05); *A23K 50/40* (2016.05); *A23K 50/42* (2016.05); *A61K 8/19* (2013.01); *A61K 8/24* (2013.01); *A61K 8/922* (2013.01); *A61K 8/9789* (2017.08); *A61K 8/9794* (2017.08); *A61K 8/986* (2013.01); *A61K 31/10* (2013.01); *A61K 31/198* (2013.01); *A61K 31/4415* (2013.01); *A61K 31/455* (2013.01); *A61K 31/51* (2013.01); *A61K 31/7008* (2013.01); *A61K 31/714* (2013.01); *A61K 31/726* (2013.01); *A61K 31/728* (2013.01); *A61Q 11/00* (2013.01); *A23V 2002/00* (2013.01); *A61K 35/00* (2013.01); *A61K 36/00* (2013.01); *A61K 38/00* (2013.01); *A61K 2035/115* (2013.01)

(58) Field of Classification Search
CPC ...... A61K 9/0056; A61K 8/19; A61K 8/9789; A61K 31/198; A61K 38/00; A61K 2035/115; A61K 8/922; A61Q 11/00; A23V 2002/00

See application file for complete search history.

(56) References Cited

U.S. PATENT DOCUMENTS

| | | |
|---|---|---|
| 5,641,536 A | 6/1997 | Lech et al. |
| 6,669,929 B1 | 12/2003 | Boyd et al. |

(Continued)

FOREIGN PATENT DOCUMENTS

| | | |
|---|---|---|
| WO | 2004039282 | 5/2004 |
| WO | 2005002464 | 1/2005 |

(Continued)

OTHER PUBLICATIONS

Ghodake et al., "Mouth Dissolving Films: Innovative Vehicle for Oral Drug Delivery," International Journal of Pharma Research & Review 2(10) 41-47, Oct. 2013.

*Primary Examiner* — Snigdha Maewall

(57) ABSTRACT

A composition and method for administering an active agent to a pet, such as a dog, a cat or a horse. The composition may comprise a yogurt-based chewable delivery matrix and a plurality of water-soluble film pieces dispersed throughout the chewable delivery matrix. The composition may also comprise a delivery matrix having at least 15% by weight of crude protein and a plurality of water-soluble film pieces dispersed throughout the delivery matrix. The plurality of water-soluble film pieces encompass an active agent therein, wherein the active agent is rapidly released from the composition upon contact with saliva from the pet. At least a portion of the released active agents may be oromucosally absorbed by the pet.

19 Claims, No Drawings

Related U.S. Application Data continuation of application No. 14/955,932, filed on Dec. 1, 2015, now Pat. No. 10,434,061.

(60) Provisional application No. 62/148,454, filed on Apr. 16, 2015, provisional application No. 62/088,313, filed on Dec. 5, 2014.

(51) Int. Cl.

| | |
|---|---|
| *A23K 20/121* | (2016.01) |
| *A23G 4/00* | (2006.01) |
| *A61K 8/92* | (2006.01) |
| *A61K 8/98* | (2006.01) |
| *A61K 8/9789* | (2017.01) |
| *A61K 8/9794* | (2017.01) |
| *A61K 38/00* | (2006.01) |
| *A61K 35/00* | (2006.01) |
| *A61K 36/00* | (2006.01) |

(56) References Cited

U.S. PATENT DOCUMENTS

| | | | |
|---|---|---|---|
| 7,641,927 B2 | 1/2010 | Gebreselassie et al. | |
| 7,763,235 B2 | 7/2010 | Boyd et al. | |
| 8,475,771 B2 | 7/2013 | Boyd et al. | |
| 8,540,823 B2 | 9/2013 | Drehs et al. | |
| 8,697,174 B2* | 4/2014 | Teconchuk | A23K 50/40 |
| | | | 426/805 |
| 2004/0136924 A1 | 7/2004 | Boyd et al. | |
| 2007/0113796 A1 | 5/2007 | Schildgen et al. | |
| 2008/0292683 A1 | 11/2008 | Sanghvi et al. | |
| 2009/0311197 A1 | 12/2009 | Romanowski et al. | |
| 2013/0273125 A1* | 10/2013 | Barnvos | A23K 10/26 |
| | | | 264/237 |

FOREIGN PATENT DOCUMENTS

| | | | |
|---|---|---|---|
| WO | 2012078134 | 6/2012 | |
| WO | 2012082101 | 6/2012 | |
| WO | 2012082103 | 6/2012 | |
| WO | 2012087326 | 6/2012 | |
| WO | WO-2012082103 A1 * | 6/2012 | A61K 8/731 |

* cited by examiner

COMPOSITION AND METHOD FOR ORALLY ADMINISTERING ONE OR MORE ACTIVE AGENTS TO A PET

PRIORITY CLAIM

This application is a continuation of U.S. patent application Ser. No. 16/537,131, filed Aug. 9, 2019, claiming priority to U.S. application Ser. No. 14/955,932 filed Dec. 1, 2015, and Provisional Application Ser. No. 62/088,313 filed on Dec. 5, 2014, and U.S. Provisional Application Ser. No. 62/148,454 filed Apr. 16, 2015, the entire contents of each are hereby incorporated by reference herein.

FIELD OF INVENTION

The present invention relates generally to chewable pet treats comprising one or more active agents. More particularly, the invention relation to the use of a chewable matrix, such as chewable treat, for delivering active agents to an animal or pet.

BACKGROUND

It may be advantageous to the health of a pet, for example, a dog or a cat, to administer a vitamin, a nutrition supplement, a pharmaceutical ingredient, or other active agents, to improve the health of the pet. Although these active agents can benefit the pet's health, it is often a difficult process to administer the active agents to the pets. These beneficial active agents have typically been provided in the form of a solid pill (e.g., tablet or gelatin capsules) or a liquid (e.g., viscous gel) that requires the pet owner to forcibly administer the pill or liquid to the pet. For example, administration of the active agents may require the pet owner to manually force open the pet's jaw, insert his hand into the pet's mouth, and force the pill or liquid down the pet's throat. This forcible oral administration of a composition is often uncomfortable and stressful for the pet and often resisted by the pet. Therefore, pet owners have had to find different ways to trick the pet to comply with such forcible oral administration. Additionally, the stress, discomfort, and resistance by the pet are particularly problematic for regular administration of 30 active agents to the pet (e.g., once daily, two daily), which requires regular and repeat stress to the pet.

Therefore, there is a continuing need in the art for orally administered compositions that can improve delivery of one or more active agents to a pet. It is therefore an object of the present invention to provide pet treat compositions comprising one or more active agents which can be easily administered to a pet.

SUMMARY OF THE INVENTION

In accordance with the foregoing objectives and others, one embodiment of the present invention provides a chewable composition formulated for oral delivery to a dog or a cat. The composition comprises a chewable delivery matrix comprising a yogurt powder, a flavoring agent palatable to the dog or cat, and water. The yogurt powder being present in at least 3% by weight of the chewable composition. The composition also comprises at least about 0.01% by weight of a plurality of water-soluble film pieces dispersed homogeneously throughout the chewable delivery matrix. The plurality of water-soluble film pieces comprise an active agent and a coloring agent therein. The active agent is rapidly releasable from the chewable composition upon contact with saliva from the dog or cat. The water in the chewable delivery matrix is in an amount selected for mixing with the plurality of water-soluble film pieces without causing aggregation of the water-soluble film pieces.

In another embodiment, a method for oral delivery of an active agent to a dog or a cat is provided. The method comprises orally administering a chewable composition comprising a delivery matrix and a plurality of water-soluble film pieces dispersed homogenously throughout the matrix. The plurality of water-soluble film pieces include the active agent therein. The method also includes rapidly dissolving a first portion of the plurality of water-soluble film pieces in a mouth of the dog or cat upon contact with saliva from the dog for or omucosal delivery of the active agent to the dog or cat. The method further includes subsequently releasing the active agent from a second portion of the plurality of water-soluble film pieces for delivery to a gastrointestinal track of the dog or cat.

In a further embodiment, a composition formulated for oral delivery to a dog or a cat is provided. The composition comprises a delivery matrix comprising at least 15% by weight of crude protein, a flavoring agent palatable to the dog or the cat, and water. The composition also comprises at least about 0.01% by weight of a plurality of water-soluble film pieces dispersed homogeneously throughout the delivery matrix, the plurality of water-soluble film pieces comprise an active agent and a coloring agent therein, the active agent being rapidly releasable from the composition upon contact with saliva from the dog or the cat. The water in the delivery 5 matrix is in an amount selected for mixing with the plurality of water-soluble film pieces without causing aggregation of the water-soluble film pieces.

These and other aspects of the invention will become apparent to those skilled in the art after a reading of the following detailed description of the invention, including the appended claims.

DETAILED DESCRIPTION

In the following description of the invention, it is to be understood that the terms used have their ordinary and accustomed meanings in the art, unless otherwise specified. The term "active agent" is intended to broadly refer to any substance administered to an individual pet to achieve a biological effect. The term "active agent" includes, without limitation, vitamins, minerals, nutritional supplements, herbal remedies, pharmaceutical agents, and the like. All weights referred to herein are given in terms of "% by weight" of the total composition, unless otherwise indicated.

An exemplary embodiment of the present invention includes a composition formulated for oral delivery to a pet (e.g., a dog, cat or horse) comprising a delivery matrix and a plurality of water-soluble film pieces dispersed therein. The water-soluble film pieces appear confetti-like and dispersed throughout the delivery matrix. Specifically, the water-soluble film pieces may be dispersed homogeneously, or substantially homogenously throughout the delivery matrix. The pet-ingestible composition may include any suitable amounts of the water-soluble film pieces. In one embodiment, the pet-ingestible composition may include at least about 0.01% by weight of water-soluble film pieces. In other embodiments the pet-ingestible composition may include up to about 0.05%, 0.1%, 0.15%, 0.2%, 0.25%, 0.3%, 0.5% or 1% by weight of the water-soluble film pieces. In some other embodiments, the pet-ingestible composition may include no more than 0.2% by weight of the water-soluble film pieces. In an alternative embodiment, the pet-ingestible composition may include no more than 1% by weight of the water-soluble film pieces.

In some embodiments, the pet-ingestible composition may comprise more than one type of water-soluble film pieces dispersed within the delivery matrix. For example, the pet ingestible composition may include a plurality of a first type of water-soluble film pieces having a first active agent and a plurality of a second type of water-soluble film pieces having a second active agent. The first type of film pieces may be colored differently from the second type of film pieces and thereby providing a clear visual distinction to the consumer that the pet 10 ingestible composition includes more than one type of film pieces for rapid release of active agents.

The water-soluble film pieces may be in the form of a thin sheet having any suitable size, thickness and shape. The water-soluble film pieces may be formed from a composition comprising any film former suitable for oral consumption by an animal, particularly, a dog, a cat or a horse. The term film former may be understood to indicate any material, which is capable, by itself or with the additional of at least one auxiliary film-forming agent, of forming a continuous film which adheres to a surface and functions as a binder for other components contained therein. The film formers can be either natural or synthetic and is typically a polymeric material. The film forming polymeric material may comprise a homopolymer or copolymer, and may be linear, branched or cross-linked, In some embodiments, the film forming polymeric material may be elastomeric, and in other embodiments, the film forming polymeric material may be thermoplastic.

Typically, the film former may comprise at least one polymer or a copolymer, which may be or may not be cross-linked. In some embodiments, the film former is hydrophilic, and more particularly, may be water-soluble. In one exemplary embodiment, the film former rapidly dissolves upon contact with a source of water, such as saliva from an animal's mouth. The film former may also be sufficiently resilient to water such that the film former will not dissolve or soften (e.g., via absorption of water from ambient air) upon storage at room temperature in ambient air for at least three months, six months, or a year, In some embodiments, the film pieces may be sensitive to change in ambient temperature and relative humidity. For example, the film pieces may degrade in the presence of oxygen or UV light. Therefore, exemplary compositions may be packaged in any suitable packaging material for providing protection during storage, transport, sale and use by the consumer. In certain exemplary embodiments, the film pieces may also be selected to provide sufficient elasticity and/or resilience such that the film pieces are capable of withstanding mixing and/or agitation of the film pieces into the delivery matrix. For example, the film pieces may be capable of withstanding agitation in a mixture for at least 10 mins, at least 15 mins, or at least 30 minutes without breaking apart.

In some exemplary embodiments, the film former may comprise one or more water-soluble polymers. The film former may include a polysaccharide, such as a starch or a gum. For example, the film former may include a natural or synthetic starch (e.g., tapioca starch, potato starch, etc.), a pectin, a natural or synthetic gum (e.g., gum arabic, sodium alginate, etc.), cellulose or a cellulose derivative (e.g., cellulose ether), and combinations thereof. Suitable starches include, for example, any starch extracted from roots, tubers, grains, seeds, and others, including but not limited to, wheat starch, corn starch, potato starch, tapioca starch, rice starch, arrowroot starch, sweet potato starch, pea starch, barley starch, maltodextrin, amylose, high amylose starch, modified starch (e.g., hydroxypropylated high amylose starch), dextrin, levan, elsinan, gluten, etc. In certain embodiments, the film former may comprise a natural or synthetic gum. Suitable natural gums include sodium alginate, gum arabic, xantham gum, gum acacia, guar gum, pullulan, agar, karaya gum, locust bean gum, carrageenan, tragacenthan and other gums. Suitable cellulose derivatives may include cellulose ethers such as methylcellulose, ethylcellulose, ethyl methyl cellulose, hydroxy ethyl cellulose, hydroypropyl cellulose, hydroxyethyl methyl cellulose hydroxypropyl methyl cellulose, ethyl hydroxyethyl cellulose, 25 carboxymethyl cellulose, etc.

In a particular embodiment, the film former may comprise a polymer, in particular, a polysaccharide. In some embodiments, the polysaccharide may be cross-linked upon formation of a film. In other embodiments, the polysaccharide is not cross-linked in the film. In certain exemplary embodiments, the film former is formed from at least one food-grade film former suitable for oral consumption by an animal. In certain embodiments, the film formers are derived from natural sources, e.g., natural starch from wheat, corn, potato, tapioca, rice, arrowroot, sweet potato, peas, barley, etc.

In certain embodiment, the film former includes a cellulose, a cellulose derivative (e.g., cellulose ether), or combinations thereof. Specifically, the cellulose and/or cellulose derivative comprise at least 1% by weight, at least 5% by weight, or at least 10% by weight of of the film pieces. In other embodiments the cellulose and/or cellulose derivative includes about 1% to about 90% by weight, about 5% to about 50% by weight, about 10% to about 40% by weight, about 20% to about 35% by weight, or about 25% to about 30% by weight of the film pieces.

The film pieces further include one or more active agents for imparting a benefit to a pet. The one or more active agents are preferably dispersed throughout the film pieces and encompassed by the film former. The active agents may be particulate and dispersed homogeneously throughout the film, or the active agents may be dissolved across the film. Suitable active agents are not particularly limited and may include any substance or mixture of substances that impart a physiological benefit to an animal, particularly a pet, such as a cat, a dog or a horse. The active agents may be included in the composition in any physiologically therapeutic effective amounts. Typically, the active agents comprise from about 5% to about 50% by weight, about 10% to about 40% by weight, about 20% to about 35% by weight, or about 25% to about 30% by weight of the film pieces. The one or more active agents are preferably distributed homogenously throughout the plurality of film pieces such that equally sized film pieces will include approximately the same amount of active agents. By approximately the same amount, it is meant within 5%, within 3% within 2% or within 1% of the amount of an active agent present within a film piece.

In one particular embodiment, the film pieces may comprise, active agents such as anti-plaque agents, anti-inflammatory agents, anti-tumor agents, anesthetics, breath freshening agents, anti-anxiety agents, energizing agents, weight loss agents, one or more vitamins and/or minerals, nutritional supplements, probiotic compositions, supplements that provide a calming effect to a pet, supplements that improves energy levels of a pet, herbal supplements to induce weight loss, starch absorption blockers, etc. In other embodiments, the active agents may be incorporated into both the delivery matrix and the film pieces. Examples of suitable active agents include sodium hexametaphosphate, vitamins (e.g., retinol palmitate (vitamin A), thiamine (vitamin B1), riboflavin (vitamin B2), niacin or niacinamide (vitamin B3), pyridoxine hydrochloride (vitamin B6), cyanobalamine (vitamin B 12), ascorbic acid (vitamin C), cholecalciferol (vitamin D3), DL-alpha Tocopheryl Acetate (vitamin E), etc.), calcium, phosphorus, potassium, chloride, magnesium, iron, copper, manganese, manganese proteinate, zinc, iodine, niacin, colbalt, glucosamine, glucosamine HCI, N-acetyl-glucosamine, chondroitin sulfate, methylsulfonylmethane, hyaluronic acid, methionine, bromelain, hyaluronic acid, 10 peptides, La-glutathione, la-glutamine, L-carnitine, L-lysine, taurine, biotin, pyridoxine, omega-3, omega-6, chlorophyll, Phaseolus Vulgaris, L-theanine, chamomile, fish oil, eicosapentaenoic acid, docosahexaenoic acid, cranberry extract, catnip, yucca root extract, diatomaceous earth, sodium bicarbonate, peppermint oil, colve oil, probiotics (e.g., Bacilius subtilis, Bacilius licheniformis), flavonoid, colostrum, etc. In some embodiments the film pieces may be substantially free or free of vitamin C. In other embodiments, the film pieces may be substantially free or free of vitamin B.

In one particular embodiment, the active agents may impart an oral care benefit, such as anti-plaque formation and breath freshening to the pet. Examples of suitable oral care active agents include yucca root extract, diatomaceous earth, sodium bicarbonate, sodium hexametaphosphate, peppermint oil, clove oil, and combinations thereof. It is believed that the oral care active agents help maintain healthy teeth and gum in the pet, in particular dogs and/or cats. In certain exemplary embodiments, one or more oral care active agents are incorporated into the film pieces. In other exemplary embodiments, one or more oral care active agents are incorporated into both the film pieces and the delivery matrix. The active agents may include particulate materials suitable for abrasion against the surface of the pet's teeth to mechanically remove plaque build-up from the teeth. The abrasive agent may be incorporated into the delivery matrix alone or may be incorporated into both the delivery matrix and the film pieces. In an exemplary embodiments, the abrasive agent comprises from about 0.1 to about 1.0% by weight of the total pet-ingestible composition. In other embodiments, the anti-plaque ingredients may include substances believed to impart a whitening effect (e.g., sodium bicarbonate) and/or a tartar prevention effect (e.g., sodium hexametaphosphate) to the teeth of the pet. The whitening agent may be from about 0.1% to about 0.5% by weight of the total pet-ingestible composition. The tartar prevention agent may also be from about 0.1% to about 0.5% by weight. The oral care active agents may further include an agent that imparts a breath freshening effect (e.g., peppermint oil, clove oil, combinations thereof, etc.) to the pet. The breath freshening agent may be from about 0.1% to about 0.5% by weight. In one exemplary embodiment, the pet-ingestible composition may comprise a plurality of oral care agents in the following amounts:

| Active Ingredient | % by Weight of Total Pet-Ingestible Composition |
| --- | --- |
| Yucca Root Extract | 5-7% |
| Diatomaceous Earth | 0.4-0.6% |
| Sodium Bicarbonate | 0.2-0.3% |
| Sodium Hexametaphosphate | 0.2-0.3% |
| Breath freshening agents | 0.1-0.3% |

In an alternative embodiment, the pet-ingestible composition may comprise a rigid delivery matrix and a plurality of oral care active agents in the following amounts:

| Active Ingredient | % by Weight of Total Pet-Ingestible Composition |
| --- | --- |
| Sodium Bicarbonate | 0.1-0.5% |
| Sodium Hexametaphosphate | 0.1-0.5% |
| Breath freshening agents | 0.1-0.3% |

In certain exemplary embodiments, compositions having a rigid delivery matrix may further include an abrasive agent. In other exemplary embodiments, compositions having a rigid delivery matrix may exclude an abrasive agent. It is believed that the rigidity of the delivery matrix may be suitable for abrasion against the surface of the pet's teeth to mechanically remove plaque build-up from the teeth.

In another embodiment, the active agents may impart a beneficial effect to the joints of the pet. In certain exemplary embodiments, one or more joint benefit active agents are incorporated into the film pieces. In other exemplary embodiments, one or more joint benefit active agents are incorporated into both the film pieces and the delivery matrix. It is believed that ingestion of various dietary supplements, such as glucosamine, chondroitin sulfate, methylsulfonylmethane, and/or anti-oxidants may impart a beneficial effect to the joints of the pet. More particularly, it is believed to improve flexibility, reduce inflammation and/or support healthy joint function in pets. It is further believed to provide beneficial effects, e.g., relief of symptoms to pets, such as dogs, suffering from arthritis. In an exemplary embodiments, the joint benefit active agents include glucosamine I-ICI and chondroitin sulfate. The glucosamine I-ICI may be obtained from any suitable source, for example, from shellfish. The chondroitin sulfate is commonly found in cartilage and may be obtained from any suitable source, such as porcine cartilage. In particular exemplary embodiment, glucosamine HCI may be present from about 10% to about 20% by weight of the total pet-ingestible composition. The chondroitin sulfate may be present from about 5% to about 15% by weight. The pet-ingestible compositions may further include additional joint benefit active agents, such as, for example, methylsulfonylmethane, and anti-oxidants (e.g., hyaluronic acid, maganese, La-glutathione), and combinations thereof. The methylsulfonylmethane may be present from about 1% to about 5% by weight. Anti-oxidants (e.g., hyaluronic acid, maganese, L-glutatione, combinations thereof, etc.) may also be present from about 0.1% to about 1% by weight. In one exemplary embodiment, the pet-ingestible composition may comprise a plurality of joint benefit active agents in the following amounts:

| Active Ingredients | % by Weight of Total Pet-Ingestible Composition |
| --- | --- |
| Glucosamine HCI | 15-18% |
| Chondroitin Sulfate | 8-12% |
| Methylsulfonylmethane | 2-3% |

-continued

| Active Ingredients | % by Weight of Total Pet-Ingestible Composition |
| --- | --- |
| Hyalurionic Acid | 0.1-0.3% |
| Maganese Proteinate | 0.1-0.2% |
| L-Glutathione | 0.01-0.05% |

In another embodiment, the active agents may impart a digestive benefit to the pet. The digestive agents may include a probiotic composition containing live (viable) naturally occurring microorganisms and/or other digestive aids. In certain exemplary embodiments, one or more digestive agents are incorporated into the film pieces. In other exemplary embodiments, 5 one or more digestive agents are incorporated into both the film pieces and the delivery matrix. It is believed that ingestion of certain microorganisms, such as probiotic bacterium, may impart a benefit, particularly a gastrointestinal benefit, to the pet, such as a dog or a cat. The probiotic agents may include any suitable bacterium that imparts a beneficial effect to a pet, particularly to a dog or a cat. More particularly, the probiotic agent may include any suitable bacterium that imparts a gastrointestinal benefit, such as, for example, improve digestion or relief from gastrointestinal discomfort, particularly for a dog. For example, the probiotic agents may include *Bacilius subtilis* (e.g., in the form of a dried *Bacilius subtilis* fermentation product), *Bacilius licheniformis* (e.g., in the form of a dried *Bacilius licheniformis* fermentation product), or combinations thereof. In certain exemplary embodiments, each pet chew composition may include at least 200 million, at least 1 billion, at least 2 billion, or at least 3 billion colony forming units (CFUs) of microrganisms. In a particular embodiment, each pet chew composition may include at least 2 billion CFUs of *Bacilius subtilis* in combination with *Bacilius licheniformis*. In an alternative exemplary embodiment, at least 200 million CFI-JS of microorganisms, preferably *Bacilius subtilis* in combination with *Bacilius licheniformis*, may be included in each 35 mg pet chew. The probiotic agents may be incorporated only in the film pieces, only in the delivery matrix, or in both the film pieces and the delivery matrix. The digestive agents may further include other digestive aids such as, compositions that promote growth of beneficial bacteria in the gastrointestinal track of the pet, for example, inulin. The digestive aids (e.g., inulin) may be incorporated only in the film pieces or in both the film pieces and the delivery matrix.

In another embodiment, the active agents may impart a calming effect to the pet, particularly to a dog or a cat. It is believed that ingestion of various dietary supplements may impart a calming effect to the pet, particularly a dog or a cat. In particular, the calming agents are believed to reduce the impact of increased environmental stressors. More typically, the calming agents are believed to reduce anxiety, nervousness, hyperactivity, frayed nerves, excess barking, abnormal urine marking, trembling, shivering, destructive behavior and/or aggressive behavior in a dog. The calming agents are believed to assist the pet, particularly dog or cat, achieve an alert state of relaxation without a drowsy effect. Examples of suitable claming agents include flavonoid, colostrum, B vitamins (e.g., Thiamine (Vitamin B 1), Niacin (Vitamin B3), Pyridoxine (Vitamin B6), Vitamin B12, etc.), L-Theanine (e.g., Suntheanine® brand), chamomile, and combinations thereof. In certain exemplary embodiments, the calming agents are incorporated into the film pieces. In other exemplary embodiments, the calming agents are incorporated into both the film pieces and the delivery matrix. The calming agents may include a combination of flavonoid and colostrum, e.g., commercially available mixture blend of flavonoid and colostrum known as FlavoCol™. The combination of flavonoid and colostrum may be present from about 0.5% to about 3% by weight of the total pet-ingestible composition. The calming agents may include one or more B vitamins. The B vitamins (e.g., Thiamine (Vitamin B1), Niacin (Vitamin B3), Pyridoxine (Vitamin B6), Vitamin B12, etc.) may be present from about 0.05% to about 1% by weight of the total pet-ingestible composition. The calming agents may also include L-theanine (e.g., Suntheanine® brand) from about 0.1% to about 1% by weight. The calming agent may further include chamomile (e.g., matricaria perforata powder) from about 0.1% to about 1% by weight. In some embodiments, the calming agents do not include L-tryptophan, and in specific exemplary embodiments, the pet-ingestible composition may be free or substantially free of la-tryptophan, In one exemplary embodiment, the pet-ingestible composition may comprise a plurality of calming agents in the following amounts:

| Active Ingredient | % by Weight of Total Pet-Ingestible Composition |
| --- | --- |
| Flavonoid and Colostrum FlavoCol ™ | 1-2% |
| Niacin (Vitamin B3) | 0.2-0.5% |
| L-Theanine Suntheanine ® brand | 0.1-0.3% |
| Chamomile (*Matricaria erforata*) Powder | 0.1-0.3% |
| Thiamine (Vitamin B I) | 0.1-0.2% |
| Pyridoxine (Vitamin B6) | 0.01-0.04% |
| Vitamin B 12 | 0.0001-0.001% |

In an alternative embodiment, the pet-ingestible composition may comprise a plurality of calming agents in the following amounts:

| Active Ingredient | % by Weight of Total Pet-Ingestible Composition |
| --- | --- |
| Flavonoid and Colostrum (FlavoCol ™) | 1-2% |
| Niacinamide | 0.5-1.5% |
| L-Theanine (Suntheanine ® brand) | 0.3-0.7% |
| Chamomile (*Matricaria perforata*) Powder | 0.1-0.3% |
| Thiamine (Vitamin B l) | 0.1-0.2% |
| Pyridoxine (Vitamin B6) | 0.01-0.04% |
| Vitamin B 12 | 0.0001-0.001% |

In a further embodiment, the active agents may control the weight (e.g., inhibit weight gain and/or induce weight loss) of a pet. In certain exemplary embodiments, one or more weight control active agents are incorporated into the film pieces. In other exemplary embodiments, one or more weight control active agents are incorporated into both the film pieces and the delivery matrix. It is believed that ingestion of various dietary supplements, such as phaseoulus vulgaris, L-taurine, and/or certain other amino acids and minerals may inhibit weight gain or induce weight loss in a pet, In an exemplary embodiments, weight control active agents include phaseoulus vulgaris and/or L-taurine. In a particular embodiment, phaseoulus vulgaris may be present from about 0.5% to about 5% by weight of the total pet-ingestible composition. The L-taurine may be present from about 0.001% to about 0.01% by weight. The pet-ingestible compositions may further include additional weight control active agents, such as, for example, L-glutamine, L-carnitine, L-lysine, manganese, thiamine and combinations thereof, In one exemplary embodiment, the pet-ingestible composition may comprise a plurality of weight control active agents in the following amounts:

| Active Ingredients | % by Weight of Total Pet-Ingestible Composition |
|---|---|
| *Phaseoulus Vulgaris* | 1-3% |
| L-Glutamine | 0.1-0.5% |
| L-Carnitine | 0.01-0.1% |
| L-Lysine | 0.01-0.1% |
| L-Taurine | 0.001-0.01% |
| Maganese | 0.001-0.01% |
| Thiamine | 0.0005-0.005% |

In another embodiment, the pet-ingestible composition may comprise film pieces having one or more vitamin, mineral and/or nutritional supplements. The pet-ingestible composition may comprise protein supplements such as yogurt powder, dried whey, and/or whey concentrate. In certain exemplary embodiments, one or more vitamin, mineral and/or nutritional supplements are incorporated into the film pieces. In other exemplary embodiments, one or more vitamin, mineral and/or nutritional supplements are incorporated into both the film pieces and the delivery matrix. In one exemplary embodiment, the pet-ingestible composition may comprise a plurality of vitamin, mineral and/or nutritional supplements in the following amounts:

| Active Ingredients | % by Weight of Total Pet-Ingestible Composition |
|---|---|
| Potassium | 0.05-0.1% |
| Chloride | 0.03-0.1% |
| Magnesium | 0.001-0.01% |
| Thiamine | 0.001-0.01% |
| Riboflavin | 0.001-0.01% |
| Niacin | 0.005-0.02% |
| Pyridoxine | 0.001-0.01% |
| Ascorbic Acid | 0.05-0.2% |
| Omega 3 Fatty Acids | 0.1-0.5% |
| Omega 6 Fatt Acids | 0.05-0.2% |

Furthermore, the composition may comprise at least 1 IU of Vitamin E per 1 to 2 grams of the pet ingestible composition.

In certain embodiments, the film pieces may include a coloring agent. The coloring agent may be visibly different from the color of the delivery matrix. More particularly, the film pieces may be colored to provide significant contrast between the film pieces and the delivery matrix, for example, the film pieces may include a coloring agent that imparts a vibrant color and in contrast, the delivery matrix may be a subdued light color. For example, the film pieces may include coloring agents that impart a red or orange color, which may be placed in contrast to a light color, e.g., white or off-white delivery matrix. Any suitable coloring agent that may be orally administered to an animal may be used. In some embodiments, the coloring agent is a food grade coloring additive. In another embodiment, the coloring agent includes spirulina, red cabbage juice and/or other naturally occurring pigments. For example, the coloring agents may include FD&C Blue No. 1 (disodium salt of ethyl [4-[p-[ethyl (m-sulfobenzyl) aminol-u-(osulfophenyl) benzylidenel-2,5-cyclohexadien-ylidenel (m-sulfobenzyl) ammonium hydroxide), FD&C Blue No. 2 (disodium salt of 2-(1,3-dihydro-3-oxo-5-sulfo-2H-indol-2ylidene)-2,3-dihydro-3-oxo-1H-indole-5-sulfonic acid (CAS Reg. No. 860-22-0)), FD&C Green No. 3 (disodium salt of N-ethyl-N-[4-[[4-[ethyl[(3-sulfophenyl) methyllaminolphenyll (4hydroxy-2-sulfophenyl) methylenel-2,5-cyclohexadien-I-ylidenel-3sulfobenzenemethanaminium hydroxide (CAS Reg. No. 2353-45-9)), Orange B (disodium salt of 1-(4-sulfophenyl)-3-ethylcarboxy-4-(4-sulfonaphthylazo)-5-hydro-xypyrazole), Citrus Red No. 2 (1-(2,5-dimethoxyphenylazo)-2-naphthol), FD&C Red No. 3 (monohydrate of 9 (o-carboxyphenyl)-6-hydroxy-2,4,5,7-tetraiodo-3H-xanthen-3-one, disodium salt), FD&C Red No. 40 (disodium salt of 6-hydroxy-5-[(2-methoxy-5-methyl-4-sulfophenyl) azol-2naphthalenesulfonic acid), FD&C Yellow No. 5 (tri sodium salt of 4,5-dihydro-5-oxo-1-(4-sulfophenyl)-4-[4-sulfophenyl-azo]-1H-pyrazole-3-carboxylic acid (CAS Reg. No. 1934-21-0)), FD&C Yellow No. 6 (disodium salt of 6-hydroxy-5-[(4-sulfophenyl)azo]-2-naphthalenesulfonic acid (CAS Reg. No. 2783-94-0)), amongst others, and combinations thereof.

In some embodiments, the film pieces may include one or more dietary fibers, such as a natural fiber, e.g., oat fiber, wheat fiber, etc. In other embodiments, the film pieces may be free of dietary fibers. It is believed that the addition of dietary fibers to the film pieces may reduce the concentration of color, and thereby mute the coloring. Thus, to maintain vibrant coloring of the film pieces, dietary fiber may be excluded. In some examples, the film pieces may be free or substantially free of dietary fibers. By substantially free it is meant that the film pieces may include small traces of dietary fiber that it does not cause any noticeable degradation of color appearance to the film pieces. In certain embodiments, the film pieces may also be translucent or semi-translucent.

The film pieces may further comprise a humectant, an emulsifier, a thickener, a lubricant, a sweetener, a surfactant, etc. Suitable humectants may include propylene glycol, glycerol, sugar alcohols (e.g., sorbitol, xylitol, maltitol), etc. Additionally, suitable emulsifiers may include polysorbate, polyethylene glycol, etc. In one exemplary embodiment, the film pieces may comprise a polysaccharide (e.g., tapioca starch), a natural gum (e.g., sodium alginate), a humectant (e.g., glycerin), an emulsifier (e.g., polysorbate), flavoring agents, and sweeteners. In one specific embodiment, the film pieces are formed from a composition comprising glycerin, flavoring agents, polysorbate, sodium alginate, sorbitol, sorbitan ester, sucralose, tapioca starch, water, and one or more active agents, In one specific embodiment, the film pieces include a combination of hydroxypropyl methylcellulose, glycerin, spirulina and one or more active agents. In another embodiment, the film pieces include a combination of hydroxypropyl methylcellulose, glycerin, red cabbage juice, sodium bicarbonate and one or more active agents. In a further embodiment, the film pieces consist essentially of or consists of a combination of hydroxypropyl methylcellulose, glycerin, spirulina, and one or more active agents. In an even further embodiment, the film pieces consist essentially of or consists of a combination of hydroxypropyl methylcellulose, glycerin, red cabbage juice, sodium bicarbonate and one or more active agents.

Upon contact with a water source, such as saliva from a pet, the film pieces may quickly dissolve and rapidly release the active agents into the surrounding environment. In some exemplary embodiments, the film pieces may fully dissolve in less than about 30 seconds, less than about 10 seconds, less than about 5 seconds, when placed in contact with saliva from the mouth of the pet.

The water-soluble film pieces may be in any suitable size and shape for dispersing in the delivery matrix and oral delivery to a pet. In particular, the water-soluble film pieces may have any suitable thickness for rapid dissolution upon contact with saliva from the pet. However, the film pieces may also be sufficiently thick that the water-soluble film pieces will 30 not dissolve, bleed color into the delivery matrix, or soften upon storage at room temperature for at least three months, six months, a year, or two years.

In one exemplary embodiment, the film pieces may be uniformly sized and shaped. The film pieces may have any suitable shape, such as an irregular shape or any geometric shape. For example, the film pieces may be in the shape of a polygon, such as triangle, quadrilateral (e.g., square, rectangle, trapezoid, etc.) pentagon, hexagon heptagon, octagon, etc., a circle, an oval, an ellipse, etc. The film pieces may be of any suitable size for oral administration to a pet. Furthermore, the film pieces may be suitably sized for incorporation into the delivery matrix without folding the film pieces onto itself. The film pieces may also be suitably sized so that the film pieces do not substantially overlapping with each other as they are dispersed within the delivery matrix, and thus, prevent aggregation of the film pieces within the composition. In a particular exemplary embodiment, the film pieces may be suitably sized and shaped such that when the film pieces are homogeneously dispersed throughout the delivery matrix, the film pieces do not come in contact with each other. In one exemplary embodiment, the film pieces may have a longest dimension from about 1/64 inch to about 3/8 inch, from about 1/32 inch to about 1/4 inch, or from about 1/16 inch to about 1/8 inch. In one particular embodiment, the film pieces are in a rectangular shape. The ratio of the width to the length of the rectangular shape may be from about 1:1 to about 1:10, from about 1:1.5 to about 1 from about 1 to about 1:6.

The film pieces may be formed by first preparing a sheet of the film forming material encompassing the one or more active agents by any suitable means. Preferably, the active agents are homogenously distributed throughout the sheet of the film forming material. The sheet may be subsequently cut to formed film pieces of any desired shape. For example, the sheet of film forming material may be cut using a cutter or a die, or otherwise shaped to smaller film pieces having the desired shape.

The pet-ingestible composition also includes a delivery matrix encompassing the plurality of film pieces containing one or more active agents. The delivery matrix may include any suitable pet product to be orally consumed by an animal, more particularly, a dog, a cat, or a horse. Exemplary embodiments of the delivery matrix may include a chewable or non-chewable treat or kibble. In a particular embodiment, the delivery matrix has a soft, chewable texture. In other embodiments, the delivery matrix is the form of a rigid pellet, such as that in pet kibble. The treat or kibble may be formulated for a dog, a cat, a horse, or any other animal. For example, the pet treat or kibble may comprise a high-protein base ingredient, such as yogurt powder or whey protein concentrate, providing nutrients to the pet. In another embodiment, the pet-ingestible composition may be in the form of a chewable bar. The chewable bar may be sized and shaped to be suitable for consumption by a dog in multiple bites. For example, the chewable bar may have a dimension of approximately 4.5 inches long, from about 1 to about 1.5 inches wide, and from about 0.5 to about 0.75 inches thick. In one example, each bar may weight at or approximately 35 grams. In a further embodiment, the delivery matrix may be rigid. Preferably, the delivery matrix is sufficiently rigid that the rigidity of the delivery matrix is suitable for abrasion against the surface of the pet's teeth to mechanically remove plaque buildup from the teeth. In one embodiment, the rigid pet-ingestible composition may have an elongate shape. For example, the elongated shaped may have a uniform or different cross section along the length of the pet-ingestible composition. In certain embodiments, the pet-ingestible composition may be cylindrical (e.g., having a uniform cross section). In other embodiments, the pet-ingestible composition may have a cross-section of any suitable geometric shape (e.g., triangle, rectangle, square, pentagon, hexagon, octagon, etc.). In another example, the rigid pet-ingestible composition may have a tubular shape. The rigid pet-ingestible compositions may be suitable as a dental stick for continuous chewing by a pet (e.g., dog). In some exemplary embodiments, the rigid pet-ingestible composition may be from about 1.5 to about 5 inches in length. The exemplary rigid pet-ingestible composition may have a width or a diameter of no more than 1.25 inches. Each rigid pet-ingestible composition may weight from about 10 grams to about 30 grams.

Typically, the pet-ingestible composition includes at least 5% by weight of crude protein, at least 8% by weight of crude protein, at least 15% by weight of crude protein, at least 25% by weight of crude protein, from about 5% to about 70% by weight of crude protein, or from about 8% to about 50% by weight of crude protein, The protein may be sourced from a variety of natural sources (e.g., yogurt, chicken, beef, liver, fish, whey, etc.). In some embodiments, the pet-ingestible composition may include at least 5% crude fat, or at least 10% crude fat. In addition, the pet-ingestible composition may include crude fiber. Preferably, the amount of crude fiber in each pet-ingestible composition is less than 3%.

In one exemplary embodiment, the pet-ingestible composition includes at least 2% by weight of yogurt powder, at least 3% by weight of yogurt powder, at least 5% by weight of yogurt powder, at least 7% by weight of yogurt powder, at least 10% by weight of yogurt powder, from about 2% to about 10% yogurt powder, from about 3% to about 7% yogurt powder, from about 7% to about 90% yogurt powder, from about 10% to about 70% yogurt powder, from about 10% to about 25% yogurt powder, or from about 15% to about 20% yogurt powder. It is believed that the inclusion of yogurt powder in a yogurt-based delivery matrix provides increased bioavailability of active agents to the pet. Specifically, it is believed that the yogurt provides a faster dissolving chewable composition as compared to other pet chew compositions and thereby releasing a larger amount of active ingredients to the mouth for oromucosal delivery. In certain exemplary embodiments, the yogurt-based matrix may be rapidly dissolving thereby releasing at least a portion of the active ingredients upon ingestion, before the composition reaches the stomach for further digestion. More particularly, the yogurt-based matrix may be soft and chewable, and is also preferably crumbly and easily dissolvable upon mixing with saliva in the pet's mouth. In some embodiments, the pet-ingestible composition is soft and chewy, but is sufficiently malleable and resilient to allow the pet to repeatedly chew (e.g., to chew at least twice or thrice before swallowing) the chewable composition and expose more film pieces to saliva from the pet's mouth.

In an another embodiment, the pet-ingestible composition may include at least 16% by weight of whey protein concentrate, at least 28% by weight of whey protein concentrate, from about 16% to about 90% yogurt powder, more typically, from about 25% to about 70% yogurt powder, from about 28% to about 60%, or from about 30% to about 55%.

In some embodiments, the delivery matrix may include a bulking agent, a binding agent, a flavoring agent, a preservative agent and/or an active ingredient for oral delivery to a pet. Any suitable bulking agent may be included in the delivery matrix, for example, the delivery matrix may include grain meals or flours (e.g., wheat flour, corn meal, rice flour etc.), cellulose, methylcellulose, amongst others. The delivery matrix may also include any suitable binding agents, such as edible oils (e.g., vegetable oil, fish oil), gelatin, yogurt, etc, Typically, the delivery matrix includes a flavoring agent that is pleasing to an animal, particularly to a dog, a cat or a horse. The flavoring agent may be any suitable flavoring additive that is palatable and desirable for consumption by a dog, a cat or a horse. Typically, the flavoring agents provide a scent or taste that attracts the dog, cat or horse to consume the composition. For example, the flavoring agent may include mint flavoring, smoke flavoring, bacon flavoring, fish flavoring, chicken, beef, liver, etc. In one exemplary embodiment, the delivery matrix may include flavoring agents such that the composition is palatable to dogs. For example, the delivery matrix may include flavoring agents such that it at least 80% palatable to dogs, meaning 80% of dogs given the composition will readily consume the composition. In other embodiments, the delivery may include flavoring agents such that it is at least 90% palatable to dogs or at least 95% palatable to dogs. In other embodiments the delivery matrix may include flavoring agents such that it is at least 80% palatable to cats, at least 90% palatable to cats, or at least 95% palatable to cats. In one exemplary embodiment, the pet treat may include a breath freshening agent and a flavoring agent such that the breath freshening agent does not mask the flavoring agent and that the delivery matrix remains at least 80% at least 90% palatable or at least 95% palatable to a dog or a cat. The delivery matrix may also include any suitable active agent, such as vitamins, nutritional supplements, herbal remedies, pharmaceutical agents, and the like, as described above. In some embodiments, the pet treat composition may be substantially free of or free of meat byproducts, artificial flavors, and/or artificial colors. In other embodiments, the chewable pet treat may be gluten-free and/or grain-free.

In certain embodiments, the delivery matrix has a water-content suitable for mixing with the water-soluble film pieces, such that the film pieces do not dissolve and/or aggregate within the composition. In one exemplary embodiment, the film pieces may include a vibrant coloring agent. Thus, the delivery matrix may have a moisture level that does not permit the coloring agent to leech from the film pieces and into the delivery matrix. For example, the delivery matrix may have a moisture level (e.g., amount of water present) of less than or equal to 25%, less than or equal to 20%, less than or equal to 18%, less than or equal to 15%, less than or equal to 14%, or less than or equal to 10%.

In a particular exemplary embodiment, the delivery matrix may comprise comprising yogurt powder, dried whey, glycerin, lecithin, maltodextrin, natural chicken flavor, potato flour, potato starch, salt, soybean oil, tapioca starch, and/or preservatives (e.g., lactic acid, mixed tocopherols, rosemary, and/or sorbic acid). In one specific embodiment, the delivery matrix comprises a combination of yogurt powder and rosemary (or rosemary extract), which is believed to act as a preservative. In some exemplary embodiments, the delivery matrix may comprise at least 8% by weight crude protein, at least 10% by weight crude fat, at most 3% by weight of crude fiber, and/or at most 14% moisture.

In another exemplary embodiment, the delivery matrix may comprise potato starch, dried whey, glycerine, potato flour, sunflower lecithin, dried yogurt, flaxseed, and/or preservatives (e.g., sorbic acid and/or phosphoric acid). In some exemplary embodiments, the delivery matrix may comprise at least 15% by weight crude protein, at least 5% by weight crude fat, at most 3% by weight of crude fiber, and/or at most 20% moisture.

In some exemplary embodiments, the delivery matrix may be prepared by combining and agitating the ingredients of the delivery matrix to form a substantially homogenously or homogeneous mixture. Typically, this mixture may be prepared in a hopper, a drum, or any other suitable equipment for distributing each ingredient of the delivery matrix formulation homogenously throughout. After the delivery matrix is well mixed, the film pieces may be added to the delivery matrix formulation mixture and the mixture is further agitated until the film pieces are homogenously distributed throughout the delivery matrix mixture. Any suitable speed and amount of time for mixing and agitating the mixture may be used. In particular, after the film pieces are added to the delivery matrix mixture the speed and amount of time for mixing and agitating may be selected to so as to prevent breakdown of the film pieces and preserve the original size and shape of the film pieces.

The mixture, including the film pieces, may be placed into an extruder and extruded to any suitable size and shape. To preserve the structure of the film pieces, the delivery matrix is preferably cold extruded using any suitable process. In one particular embodiment, the composition may be formed, e.g., extruded to arrive at uniformly shaped and sized solid formulations having a size suitable for oral administration to a pet, such as a dog, a cat, or a horse, such that it is safe for the pet to ingest. In particular, the pet-ingestible compositions may be sized to be of a sufficiently large size so that it does not pose a choking hazard to the pet. In other embodiments, the pet-ingestible composition is larger than at least a tooth of the pet such that it is sized for repeat chewing by the pet. In another exemplary embodiment, the composition may be a pet chew extruded to have a weight from about 2 grams to 8 grams, or from 3 grams to 5 grams, or approximately 4 grams.

Alternatively, the delivery matrix mixture may be extruded using a heated process to any suitable size and shape, in particular, in the shape of a bar or a stick. For example, the delivery matrix may be formed into a chewable bar. The chewable bar may be sized and shaped to be suitable for consumption by a dog in multiple bites. In one example, each bar may weight at or approximately 35 grams. In another example, the chewable bar may have a dimension of approximately 4.5 inches long, from about I to about 1.5 inches wide, and from about 0.5 to about 0.75 inches thick. In a further embodiment, the delivery matrix mixture may be formed into an elongated shape. In some exemplary embodiments, the elongated shape may have a length from about 1.5 to about 5 inches. The exemplary rigid pet-ingestible composition may have a width or a diameter of no more than 1.25 inches. Each pet-ingestible composition having an elongated shape may weight from about 10 grams to about 30 grams. In some embodiments, the extruded delivery matrix mixture may be rigid, such as a dental stick for continuous chewing by a pet (e.g., dog). The delivery matrix may be hot extruded using any suitable process. In certain embodiments, the temperature at which the hot extrusion is conducted does not denature the proteins within the delivery matrix mixture or cause degradation of (e.g., melting, changing color, leeching coloring agents from) the film former pieces. In one particular embodiment, the delivery matrix is hot extruded using a process that heats the delivery matrix mixture to a temperature no greater than 2840 F or 1400 C for no more than about 6 to about 8 seconds. The delivery matrix mixture is forced through an opening in a die to form an elongated shape. The elongated shape may subsequently be cut to a desired length (e.g., from about 1.5 to about 5 inches), typically, as the extruded mixture leaves the die. In one particular embodiment, the composition may be formed, e.g., extruded to arrive at uniformly shaped and sized solid formulations having a size suitable for oral administration to a pet, such as a dog, a cat, or a horse, such that it is safe for the pet to ingest. In particular, the pet-ingestible compositions may be sized to be of a sufficiently large size so that it is larger than the size of the pet's mouth. In particular, the pet-ingestible composition is sized and shaped such that the entire composition does not fully fit within the pet's mouth and that repeated bites or chewing is necessary for the pet to consume the entire composition, More particularly, the composition may be formed into a chewable bar that is extruded, typically using a hot-extrusion process, to have a weight from about 20 grams to 40 grams, or approximately 35 grams, In another embodiment, the delivery matrix mixture may be extruded, typically using a hot-extrusion process, into a rigid composition having an elongated shape (e.g., a stick).

The pet-ingestible compositions of the present invention provides two step delivery of active agents to a pet (e.g., a dog, a cat or a horse): (1) initial rapid release and oromucosal delivery of the active agents; and (2) subsequent absorption of additional active agents via the gastrointestinal track, It is believed that this two step delivery provides improved delivery and/or availability of active agents to the pet.

First, the pet-ingestible composition of the present invention allows for delivery of active agents to the pet without significant force or struggle. The pet owner may simply offer the composition to the pet, and the pet may voluntarily consume and chew on the composition. Once the pet-ingestible composition is orally administered to the pet, saliva from the pet's mouth may come in contact with the film pieces and rapidly dissolve the film pieces, and thus rapidly releasing the active agents into the pet's mouth. In embodiments where the delivery matrix is a chewable formulation, the pet may continue to chew on the composition and thereby exposing film pieces located within the interior of the composition to the saliva of the pet and causing further dissolution of the film pieces and additional release of the active agents into the pet's mouth. The released active agents may be swallowed and subsequently absorbed by the pet through its gastrointestinal track. In some embodiments, the released active agents may also be oromucosally absorbed by the mouth of the pet. In other embodiments, the released active agents act within the pet's mouth, for example, an anti-plaque agent may impart a benefit to the teeth of the pet.

Secondly, the film pieces allow for an initial rapid release and oromucosal delivery of the active agent so that the active agent may be more rapidly absorbed by the pet. It is believed that the initial rapid release and oromucosa[ delivery may improve the overall absorption of the active agents by the pet. Specifically, oromucosal absorption of certain nutritional supplements are believed to be 9 times more effective than absorption of the same supplements via the gastrointestinal track. (See Ghodake et al., "Mouth Dissolving Films: Innovative Vehicle for Oral Drug Delivery," International Journal of Pharma Research & Review, 2(10): 41-47 (October 2013, which is incorporated by reference herein)). Therefore, the initial release of active agents from the film formers and into the mouth of the pet may provide faster absorption and increased availability of the active agents to the pet.

EXAMPLE I

An Exemplary Dog Oral Care Composition

In one exemplary embodiment, the pet treat composition may be useful for imparting a dental benefit to the dog, particularly the pet treat composition may be chewable and include one or more oral care active agents that may impart an anti-plaque, whitening and/or breath freshening effect to the pet. The chewable pet treat composition may also include a flavoring agent and is palatable to a dog. In a particular exemplary embodiment, the pet treat composition is approximately 4 grams and may include active ingredients in the following amounts:

| Active Ingredients | Amounts in 4 g Chewable Pet Treat Composition |
| --- | --- |
| Yucca Root Extract | 25 mg |
| Diatomaceous Earth | 20 m |
| Sodium Bicarbonate | 10 mg |
| Sodium Hexametaphosphate | 10 mg |
| Peppermint Oil | 5 mg |
| Clove Oil | 3 mg |

The remainder of the weight may comprise inactive ingredients, such as, yogurt flour, whey, glycerin, lactic acid, lecithin, maltodextrin, mixed tocopherols, natural chicken flavor, potator flour, potato starch, rosemary, salt, soybean oil, sorbic acid, spirulina, and tapioca starch. In some examples, spirulina may be replaced with red cabbage juice, which may be used with or without sodium bicarbonate. The chewable pet treat composition may include at least 8% by weight of crude protein, at least 10% by weight of crude fat, at most 3% by weight of crude fiber, and at most 14% by weight of moisture.

EXAMPLE II

An Alternative Exemplary Dog Oral Care Composition

In an alternative exemplary embodiment, a pet ingestible composition may imparting a dental benefit to the dog, particularly the composition may include one or more oral care active agents that may impart an anti-plaque, whitening and/or breath freshening effect to the pet. The delivery matrix may be rigid and have an elongated shape. Preferably, the delivery matrix is sufficiently rigid that the rigidity of the delivery matrix is suitable for abrasion against the surface of the pet's teeth to mechanically remove plaque build-up from the teeth. The pet ingestible composition may also include a flavoring agent and is palatable to a dog. In a particular exemplary embodiment, the pet ingestible composition is from about 10 grams to about 30 grams in weight and may comprise potato starch, glycerin, dried yogurt, potato flour, sunflower lecithin, natural chicken flavor, lactic acid, sodium bicarbonate, sorbic acid, peppermint oil, riboflavin supplement, clove oil, and sodium hexametaphosphate. The pet ingestible composition may include at least 5% by weight of crude protein, at least 5% and at most 9% by weight of crude fat, at most 2% by weight of crude fiber, and at most 18% by weight of moisture.

EXAMPLE III

An Exemplary Dog Joint Health Composition

In one exemplary embodiment, the pet treat composition may be useful for imparting a benefit to the joints of a dog, particularly the pet treat composition may be chewable and include one or more active agents that may impart a beneficial effect to the joints of a dog. The chewable pet treat composition may also include a flavoring agent and is palatable to a dog, In a particular exemplary embodiment, the pet treat is approximately 4 grams and may include active ingredients in the following amounts:

| Active Ingredients | Amounts in 4 g Chewable Pet Treat Composition |
| --- | --- |
| Glucosamine HCl | 650 mg |
| Chondroitin Sulfate | 400 mg |
| Methylsulfonylmethane | 100 m |
| Hyalurionic Acid | 10 mg |
| Maganese Proteinate | 5 mg |
| L-Glutathione | 2 mg |

The remainder of the weight may comprise inactive ingredients, such as, yogurt flour, whey, glycerin, lactic acid, lecithin, maltodextrin, mixed tocopherols, natural chicken flavor, potato flour, potato starch, rosemary, salt, soybean oil, sorbic acid, spirulina, and tapioca starch. In some examples, spirulina may be replaced with red cabbage juice, which may be used with or without sodium bicarbonate. The chewable pet treat composition may include at least 8% by weight of crude protein, at least 10% by weight of crude fat, at most 3% by weight of crude fiber, and at most 14% by weight of moisture.

EXAMPLE IV

An Exemplary Dog Probiotic Composition

In one exemplary embodiment, the pet treat composition may be useful for imparting a digestive benefit to a dog, particularly the pet treat composition may be chewable and include one or more active digestive agents that may impart a digestive benefit to a dog. Specifically, the digestive agents may include probiotic bacterium and inulin. The probiotic bacterium may be *Bacilius subtilis* (e.g., in the form of a dried *Bacilius subtilis* fermentation product), *Bacillus licheniformis* (e.g., in the form of a dried *Bacilius licheniformis* fermentation product), or combinations thereof. In a particular exemplary embodiment, the pet treat is approximately 4 grams and may include at least 2 billion CFUs *Bacilius subtilis* in combination with *Bacillus licheniformis* and 200 mg of inulin, The remainder of the weight may comprise inactive ingredients, such as, yogurt flour, whey, glycerin, lactic acid, lecithin, maltodextrin, mixed tocopherols, natural chicken flavor, potato flour, potato starch, rosemary, salt, soybean oil, sorbic acid, spirulina, and tapioca starch. In some examples, spirulina may be replaced with red cabbage juice, which may be used with or without sodium bicarbonate. The chewable pet treat composition may include at least 8% by weight of crude protein, at least 10% by weight of crude fat, at most 3% by weight of crude fiber, and at most 14% by weight of moisture.

EXAMPLE V

An Alternative Exemplary Dog Probiotic Composition

In an alternative exemplary embodiment, a pet ingestible bar composition may be useful for imparting a digestive benefit to a dog, particularly the pet ingestible bar composition may be chewable and include one or more active digestive agents that may impart a digestive benefit to a dog. Specifically, the digestive agents may include probiotic bacterium and inulin. The probiotic bacterium may be *Bacilius subtilis* (e.g., in the form of a dried *Bacilius subtilis* fermentation product), *Bacilius licheniformis* (e.g., in the form of a dried *Bacilius licheniformis* fermentation product), or combinations thereof. In a particular exemplary embodiment, the pet ingestible bar composition is approximately 35 grams and may include at least 200 million CFUs *Bacilius subtilis* in combination with *Bacilius licheniformis* and 1500 mg of inulin. The pet ingestible bar composition may further include at least 50 mg of Omega 3 fatty acids and/or at least 20 mg of Omega 6 fatty acids. The remainder of the weight may comprise inactive ingredients, such as, potato starch, whey protein concentrate, glycerin, potato flour, dried yogurt, sunflower lecithin, flaxseed meal, natural chicken flavor, sorbic acid and phosphoric acid. The pet ingestible bar composition may include at least 15% by weight of crude protein, at least 5% by weight of crude fat, at most 3% by weight of crude fiber, and at most 20% by weight of moisture.

EXAMPLE VI

An Exemplary Dog Calming Composition

In another exemplary embodiment, the pet treat composition may be useful for imparting a calming effect to a dog, particularly the pet treat composition may be chewable and include one or more calming agents that may reduce anxiety, nervousness, hyperactivity, frayed nerves, excess barking, abnormal urine marking, trembling, shivering, destructive behavior and/or aggressive behavior in a dog. The chewable pet treat composition may also include a flavoring agent and is palatable to a dog. In a particular exemplary embodiment, the pet treat is approximately 4 grams and may include active ingredients in the following amounts:

| Active Ingredients | Amounts in 4 g Chewable Pet Treat Composition |
| --- | --- |
| Flavonoid and Colostrum FlavoCol ™ | 60 mg |
| Niacin (Vitamin B3) | 13 mg |
| L-Theanine (Suntheanine ® brand) | 10 mg |
| Chamomile (*Matricaria perforata*) Powder | 10 mg |
| Thiamine (Vitamin B1) | 6 mg |
| Pyridoxine (Vitamin B6) | 1 mg |
| Vitamin B12 | 2.4 mcg |

The remainder of the weight may comprise inactive ingredients, such as, yogurt flour, whey, glycerin, lactic acid, lecithin, maltodextrin, mixed tocopherols, natural chicken flavor, potato flour, potato starch, rosemary, salt, soybean oil, sorbic acid, spirulina, and tapioca starch. In some examples, spirulina may be replaced with red cabbage juice, which may be used with or without sodium bicarbonate. The chewable pet treat composition may include at least 8% by weight of crude protein, at least 10% by weight of crude fat, at most 3% by weight of crude fiber, and at most 14% by weight of moisture.

EXAMPLE VII

An Alternative Exemplary Dog Calming Composition

In another exemplary embodiment, a pet ingestible bar composition may be useful for imparting a calming effect to a dog, particularly the pet ingestible bar composition may be chewable and include one or more calming agents that may reduce anxiety, nervousness, hyperactivity, frayed nerves, excess barking, abnormal urine marking, trembling, shivering, destructive behavior and/or aggressive behavior in a dog. The pet ingestible bar composition may also include a flavoring agent and is palatable to a dog, In a particular exemplary embodiment, the pet ingestible bar composition is approximately 35 grams and may include active ingredients in the following amounts:

| Active Ingredients | Amounts in 35 g Chewable Bar Composition |
|---|---|
| Flavonoid and Colostrum (FlavoCol ™) | 500 mg |
| Niacinamide | 400 mg |
| L-Theanine (Suntheanine ® brand) | 175 mg |
| Chamomile (*Matricaria perforate*) Powder | 200 mg |
| Thiamine (Vitamin B1) | 55 mg |
| Pyridoxine (Vitamin B6) | 8 mg |
| Vitamin B12 | 15 mcg |

The remainder of the weight may comprise inactive ingredients, such as, potato starch, dry whey, glycerine, potato flour, sunflower lecithin, dried yogurt, flaxseed meal, natural chicken flavor, green tea extract, sorbic acid, and phosphoric acid. The pet ingestible bar composition may include at least 15% by weight of crude protein, at least 5% by weight of crude fat, at most 3% by weight of crude fiber, and at most 20% by weight of moisture.

EXAMPLE VIII

An Exemplary High Protein Composition

In one exemplary embodiment, a pet ingestible bar composition may provide a high protein dietary treat to a dog. For example, the pet ingestible bar composition may include at least 25% protein. The pet ingestible bar composition may also include a flavoring agent and is palatable to a dog. In a particular exemplary embodiment, the pet treat is approximately 35 grams and may include a number of vitamins and dietary supplements in the following amounts:

| Active Ingredients | Amounts in 35 g Chewable Bar Composition |
|---|---|
| Crude Protein | at least 25% |
| Crude Fat | at most 5% |
| Crude Fiber | at most 3% |
| Moisture | at most 20% |
| Potassium | at least 20 mg |
| Chloride | at least 15 mg |
| Magnesium | at least 3 mg |
| Vitamin E | at least 30 IU |
| Thiamine | at least 3 mg |
| Riboflavin | at least 2 mg |

| Active Ingredients | Amounts in 35 g Chewable Bar Composition |
|---|---|
| Niacin | at least 5 mg |
| Pyridoxine | at least 2 mg |
| Ascorbic Acid | at least 50 mg |
| Omega 3 Fatty Acids | at least 100 mg |
| Omega 6 Fatty Acids | at least 50 mg |

For example, the pet ingestible bar composition may comprise whey protein concentrate, potato starch, glycerin, potato flour, dried yogurt, sunflower lecithin, flaxseed meal, natural chicken flavor, sorbic acid, phosphoric acid, chondroitin sulfate (e.g., porcine source), isoleucine, leucine, valine, dried beet, Vitamin E Supplement, ascorbic acid, L-carnitine, green tea extract, potassium chloride, magnesium sulfate, salt, niacinamide, riboflavin supplement, thiamine hydrochloride, and pyridoxine hydrochloride.

EXAMPLE IX

An Exemplary Weight Management Composition

In one exemplary embodiment, a pet ingestible bar composition may provide a dietary composition that is formulated to control the weight of or induce weight loss of a dog. The pet ingestible bar composition may include a flavoring agent and is palatable to a dog. The pet ingestible bar may be formulated to provide a sufficient level of nutrients to the dog, but with a reduced caloric level to help control the weight of or help weight loss of the dog. In a particular exemplary embodiment, the pet ingestible bar composition is approximately 35 grams and may include active ingredients in the following amounts:

| Active Ingredients | Amounts in 35 g Chewable Bar Composition |
|---|---|
| *Phaseoulus Vulgaris* | 500 mg |
| L-Glutamine | 100 mg |
| L-Carnitine | 20 mg |
| L-L sine | 20 mg |
| L-Taurine | 2 mg |
| Maganese | 1.5 mg |
| Thiamine | 0.5 mg |
| Potassium | 0.002 mg |
| Omega 3 fatty acids | at least 75 mg |
| Omega 6 fatty acids | at least 25 mg |

The active ingredients may further include biotin in an amount suitable for consumption by a pet (e.g., dog, cat or horse). The remainder of the weight may comprise inactive ingredients, such as, potato starch, dried whey, glycerine, potato flour, sunflower lecithin, dried yogurt, flaxseed meal, natural chicken flavor, sorbic acid, and phosphoric Acid. The pet ingestible bar composition may include at least 15% by weight of crude protein, at least 5% by weight of crude fat, at most 3% by weight of crude fiber, and at most 20% by weight of moisture.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A chewable composition formulated for oral delivery to a dog or a cat comprising:
   a chewable delivery matrix comprising a protein, the protein being at least 3% by weight of the chewable composition, a flavoring agent palatable to the dog or the cat, and water; and
   at least about 0.01% by weight of a plurality of water-soluble film pieces dispersed homogeneously throughout the chewable delivery matrix, the plurality of water-soluble film pieces comprise an active agent and a coloring agent therein, the active agent being rapidly releasable from the chewable composition upon contact with saliva from the dog or the cat,
   wherein the water in the chewable delivery matrix is in an amount selected for mixing with the plurality of water-soluble film pieces without causing aggregation of the water-soluble film pieces.

2. The composition of claim 1, wherein the amount of water in the chewable delivery matrix is less than 15% by weight of the chewable composition.

3. The composition of claim 1, wherein the water-soluble film pieces comprise a film-forming polysaccharide.

4. The composition of claim 3, wherein the film-forming polysaccharide is a natural starch.

5. The composition of claim 1, wherein the active agent comprises at least one selected from the group consisting of vitamins, minerals, nutritional supplements, herbal remedies, and pharmaceutical agents.

6. The composition of claim 5, wherein the active agent comprise at least one selected from the group consisting of anti-plaque agents, anti-inflammatory agents, anti-tumor agents, anesthetics, breath freshening agents, anti-anxiety agents, energizing agents, weight loss agents, vitamins, minerals, and probiotic compositions.

7. The composition of claim 1, wherein the chewable delivery matrix further comprises the same active agent as the film pieces or an additional active agent.

8. The composition of claim 7, wherein the additional active agent comprises at least one selected from the group consisting of vitamins, minerals, nutritional supplements, herbal remedies, and pharmaceutical agents.

9. The composition of claim 1, wherein the chewable delivery matrix further comprises an abrasive agent for mechanically scrubbing against the teeth of the pet.

10. The composition of claim 9, wherein the active agent comprises sodium hexametaphosphate.

11. The composition of claim 3, wherein the water-soluble film pieces further comprises at least one of a natural gum, a humectant, and an emulsifier.

12. The composition of claim 1, wherein the water-soluble film pieces are uniformly sized and shaped.

13. The composition of claim 12, wherein the water-soluble film pieces are rectangular.

14. The composition of claim 13, wherein a ratio of a width to a length of the rectangular shape is about 1:1 to about 1:10.

15. The composition of claim 1, wherein the water-soluble film pieces have a thickness such that the coloring agent does not leech from the water-soluble film pieces into the chewable delivery matrix.

16. The composition of claim 1, wherein the water-soluble film pieces are substantially free of dietary fiber.

17. The composition of claim 1, wherein the water-soluble film pieces comprise from about 5% to about 50% by weight of the active agent.

18. The composition of claim 1, wherein the chewable delivery matrix is substantially free of meat byproducts, gluten or grain.

19. The composition of claim 1, wherein the chewable delivery matrix further comprises rosemary or rosemary extract.

* * * * *